United States Patent
Beech et al.

(10) Patent No.: US 11,412,959 B2
(45) Date of Patent: Aug. 16, 2022

(54) EAB SENSING DEVICES WITH BIOFLUID SAMPLE CONCENTRATION

(71) Applicant: Epicore Biosystems, Inc., Cambridge, MA (US)

(72) Inventors: Robert Beech, Cincinnati, OH (US); Gavi Begtrup, Cincinnati, OH (US); Jason Heikenfeld, Cincinnati, OH (US); Jacob A. Bertrand, Montgomery, OH (US)

(73) Assignee: Epicore Biosystems, Inc., Cambridge, MA (US)

( * ) Notice: Subject to any disclaimer, the term of this patent is extended or adjusted under 35 U.S.C. 154(b) by 535 days.

(21) Appl. No.: 16/484,989

(22) PCT Filed: Feb. 7, 2018

(86) PCT No.: PCT/US2018/017199
§ 371 (c)(1),
(2) Date: Aug. 9, 2019

(87) PCT Pub. No.: WO2018/148261
PCT Pub. Date: Aug. 16, 2018

(65) Prior Publication Data
US 2020/0155046 A1    May 21, 2020

Related U.S. Application Data

(60) Provisional application No. 62/457,604, filed on Feb. 10, 2017.

(51) Int. Cl.
*A61B 5/145*    (2006.01)
*A61B 5/00*    (2006.01)
(Continued)

(52) U.S. Cl.
CPC ........ *A61B 5/14521* (2013.01); *A61B 5/0053* (2013.01); *A61B 5/01* (2013.01);
(Continued)

(58) Field of Classification Search
CPC .. A61B 5/145; A61B 5/00; A61B 5/01; A61B 5/1477; A61B 5/4266;
(Continued)

(56) References Cited

U.S. PATENT DOCUMENTS

2015/0208985 A1* 7/2015 Huang ................ A61B 5/685
156/60
2016/0278638 A1* 9/2016 Schwartz ............ A61B 5/002
2020/0196925 A1* 6/2020 Lin .................... A61B 5/14539

FOREIGN PATENT DOCUMENTS

WO    WO-2016049019 A1 * 3/2016 ......... A61B 5/14517

* cited by examiner

*Primary Examiner* — Eric J Messersmith
(74) *Attorney, Agent, or Firm* — MacMillan, Sobanski & Todd, LLC

(57) ABSTRACT

The present invention provides a biofluid sensing device capable of concentrating a biofluid sample with respect to a target analyte, so that the analyte can be accurately detected or measured by EAB sensors. Methods for using such a device provide qualitative information about the presence of the analyte, and/or quantitative information about relative concentrations of the analyte in the biofluid. The disclosed device includes a concentration channel for concentrating the biofluid sample, as well as a selectively permeable membrane, one or more EAB sensors, and one or more secondary sensors carried on a water-impermeable substrate. A method for using the disclosed device to collect a biofluid sample, concentrate the sample relative to a target analyte, and measure the target analyte is also disclosed.

23 Claims, 8 Drawing Sheets

(51) Int. Cl.
*A61B 5/01* (2006.01)
*A61B 5/1477* (2006.01)
(52) U.S. Cl.
CPC ........ *A61B 5/1477* (2013.01); *A61B 5/14546* (2013.01); *A61B 5/4266* (2013.01); *A61B 5/6833* (2013.01)
(58) Field of Classification Search
CPC ............ A61B 5/14546; A61B 5/14521; A61B 5/0053; A61B 5/6833; A61B 5/053
See application file for complete search history.

EAB SENSING DEVICES WITH BIOFLUID SAMPLE CONCENTRATION

CROSS-REFERENCE TO RELATED APPLICATIONS

The present application claims priority to PCT/US18/17199, filed Feb. 7, 2018, and U.S. Provisional Application No. 62/457,604, filed Feb. 10, 2017; and has specification that builds upon PCT/US16/58356, filed Oct. 23, 2016 and PCT/US16/58357 filed Oct. 23, 2016, the disclosures of which are hereby incorporated herein by reference in their entirety.

BACKGROUND OF THE INVENTION

Despite the many ergonomic advantages of perspiration (sweat) compared to other biofluids (particularly in "wearable" devices), sweat remains an underutilized source of biomarker analytes compared to the established biofluids: blood, urine, and saliva. Upon closer comparison to other non-invasive biofluids, the advantages may even extend beyond ergonomics: sweat might provide superior analyte information. Several challenges, however, have kept sweat from occupying its place among the preferred clinical biofluids. These challenges include very low sample volumes (nL to μL), unknown concentration due to evaporation, filtration and dilution of large analytes, mixing of old and new sweat, and the potential for contamination from the skin surface. Rapid progress in "wearable" sweat sampling and sensing devices has resolved several of the historical challenges. However, this progress has also been limited to high concentration analytes (μM to mM) sampled at high sweat rates (>1 nL/min/gland) found in, for example athletic applications. Advancements will be much more challenging as biosensing moves towards detection of large, low concentration analytes (nM to pM and lower).

For example, many known sensor technologies for detecting larger molecules are ill-suited for use in wearable sweat sensing, which requires sensors that permit continuous or extended use on a wearer's skin. Sensor modalities that require complex microfluidic manipulation, the addition of reagents, or the use of limited shelf-life components, such as antibodies, are therefore not preferred for sweat sensing. Instead, electrochemical aptamer-based ("EAB") sensor technology promises to provide stable, reliable, reagentless sensors that are sensitive to target analytes in sweat, and specific enough to produce high predictive values during the lifespan of the sensor. Such EAB sensors include multiple-capture EAB biosensors ("MCAS") disclosed in U.S. Pat. Nos. 7,803,542 and 8,003,374, and docked aptamer EAB biosensors (DAS) disclosed in U.S. Provisional Application No. 62/523,835, filed Jun. 23, 2017, each of which is hereby incorporated by reference herein in its entirety.

While EAB sensors present many advantages for wearable sensing, the low sweat concentrations of many analytes of interest present a central difficulty for such sensors, as many analytes will not naturally exist in sweat in sufficient molarities to be detected by EAB sensors. What is needed, therefore, are devices and methods that concentrate target analytes in a biofluid sample so that EAB sensors can provide useful measurements for such low concentration analytes. Such devices and methods are the subject of the present disclosure.

Many of the other challenges to successful biofluid sensor development can be resolved by creating novel and advanced interplays of chemicals, materials, sensors, electronics, microfluidics, algorithms, computing, software, systems, and other features or designs, in a manner that affordably, effectively, conveniently, intelligently, or reliably brings biofluid to sensors and sample preparing or concentrating subsystems.

SUMMARY OF THE INVENTION

The present invention provides a biofluid sensing device capable of concentrating a biofluid sample with respect to a target analyte, so that the analyte can be accurately detected or measured by EAB sensors. Methods for using such a device provide qualitative information about the presence of the analyte, and/or quantitative information about relative concentrations of the analyte in the biofluid. The disclosed device includes a concentration channel for concentrating the biofluid sample, as well as a selectively permeable membrane, one or more EAB sensors, and one or more secondary sensors carried on a water-impermeable substrate. A method for using the disclosed device to collect a biofluid sample, concentrate the sample relative to a target analyte, and measure the target analyte is also disclosed.

BRIEF DESCRIPTION OF THE DRAWINGS

The objects and advantages of the present invention will be further appreciated in light of the following detailed descriptions and drawings in which.

DEFINITIONS

Figure 1A:
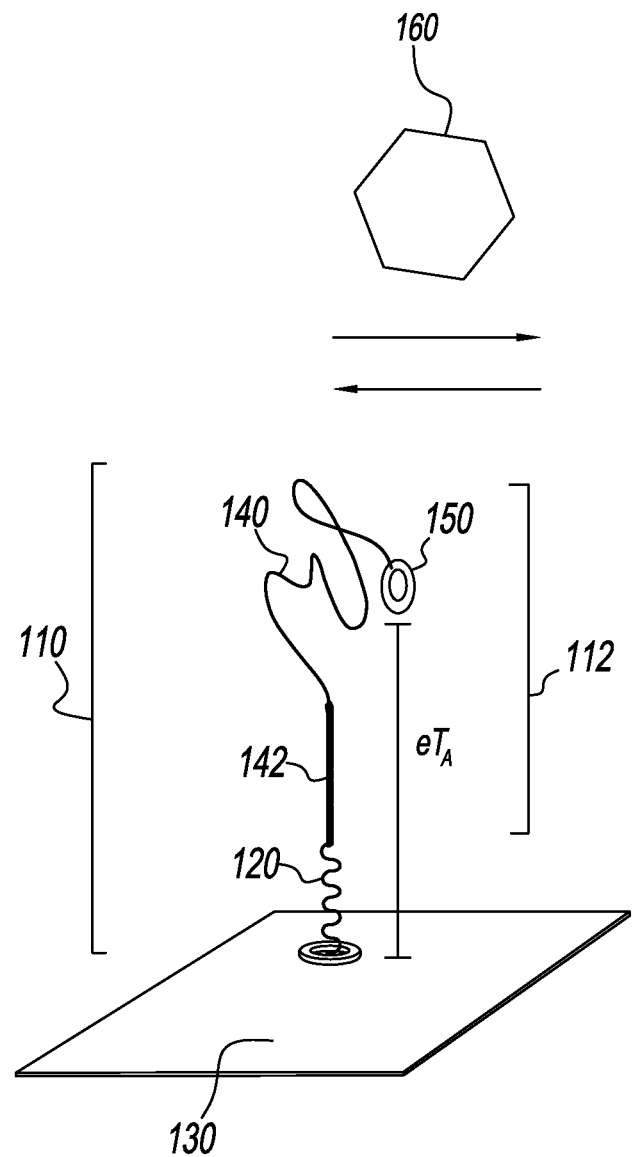
FIGS. 1A and 1B are representations of a previously-disclosed aptamer sensing element.

Before continuing with the background, a variety of definitions should be made, these definitions gaining further appreciation and scope in the detailed description and embodiments of the present disclosure.

As used herein, "sweat" means a biofluid that is primarily sweat, such as eccrine or apocrine sweat, and may also include mixtures of biofluids such as sweat and blood, or sweat and interstitial fluid, so long as advective transport of the biofluid mixtures (e.g., flow) is primarily driven by sweat.

As used herein, "biofluid" may mean any human biofluid, including, without limitation, sweat, interstitial fluid, blood, plasma, serum, tears, and saliva.

"Biofluid sensor" means any type of sensor that measures a state, presence, flow rate, solute concentration, solute presence, in absolute, relative, trending, or other ways in a biofluid. Biofluid sensors can include, for example, potentiometric, amperometric, impedance, optical, mechanical, antibody, peptide, aptamer, or other means known by those skilled in the art of sensing or biosensing.

"Analyte" means a substance, molecule, ion, or other material that is measured by a biofluid sensing device.

"Measured" can imply an exact or precise quantitative measurement and can include broader meanings such as, for example, measuring a relative amount of change of something. Measured can also imply a binary or qualitative measurement, such as 'yes' or 'no' type measurements.

"Chronological assurance" means the sampling rate or sampling interval that assures measurement(s) of analytes in a biofluid in terms of the rate at which measurements can be made of new biofluid analytes emerging from the body. Chronological assurance may also include a determination of the effect of sensor function, potential contamination with previously generated analytes, other fluids, or other measurement contamination sources for the measurement(s). Chronological assurance may have an offset for time delays in the body (e.g., a well-known 5- to 30-minute lag time between analytes in blood emerging in interstitial fluid), but the resulting sampling interval is independent of lag time, and furthermore, this lag time is inside the body, and therefore, for chronological assurance as defined above and interpreted herein, this lag time does not apply.

"EAB sensor" means an electrochemical aptamer-based biosensor that is configured with multiple aptamer sensing elements that, in the presence of a target analyte in a fluid sample, produce a signal indicating analyte capture, and which signal can be added to the signals of other such sensing elements, so that a signal threshold may be reached that indicates the presence or concentration of the target analyte. Such sensors can be in the forms disclosed in U.S. Pat. Nos. 7,803,542 and 8,003,374 (the "Multi-capture Aptamer Sensor" (MCAS)), or in U.S. Provisional Application No. 62/523,835 (the "Docked Aptamer Sensor" (DAS)).

"Biofluid sensor data" means all the information collected by biofluid sensing device sensor(s) and communicated to a user or a data aggregation location.

"Sweat stimulation" is the direct or indirect causing of sweat generation by any external stimulus, the external stimulus being applied to stimulating sweat. One example of sweat stimulation is the administration of a sweat stimulant such as pilocarpine or carbachol. Going for a jog, which stimulates sweat, is only sweat stimulation if the subject is jogging for the purpose of stimulating sweat.

"Sweat generation rate" is the rate at which sweat is generated by the sweat glands themselves. Sweat generation rate is typically measured by the flow rate from each gland in nL/min/gland. In some cases, the measurement is then multiplied by the number of sweat glands from which the sweat is being sampled.

"Sweat volume" is the fluidic volume in a space that can be defined multiple ways. Sweat volume may be the volume that exists between a sensor and the point of generation of sweat or a solute moving into or out of sweat from the body or from other sources. Sweat volume can include the volume that can be occupied by sweat between: the sampling site on the skin and a sensor on the skin where the sensor has no intervening layers, materials, or components between it and the skin; or the sampling site on the skin and a sensor on the skin where there are one or more layers, materials, or components between the sensor and the sampling site on the skin.

"Microfluidic components" are channels in polymer, textiles, paper, or other components known in the art of microfluidics for guiding movement of a fluid or at least partial containment of a fluid.

"Flow rate sensing component", is any component or components which measure the flow rate of biofluid in at least one portion of a biofluid sensing or collecting device.

"Biofluid conductivity" means measurements of the electrical conductivity of a biofluid. Biofluid conductivity serves as a means of estimating soluble anion content in the biofluid. The biofluid sensing device would measure biofluid conductivity by means of an electrode.

"Galvanic skin response" (GSR) means measurements of the electrical conductivity of the skin. GSR serves as a means of estimating sweat rate, since skin conductivity is dominated by the contribution of sweat, and increases linearly with increases in sweat rate throughout the linear range of 0.4 $\mu L/cm^2/min$ to 1.5 $\mu L/cm^2/min$.

"Sensitivity" means the change in output of the sensor per unit change in the parameter being measured. The change may be constant over the range of the sensor (linear), or it may vary (nonlinear).

"Recovery interval" means the time required for an aptamer sensing element to release a target analyte back into solution and return to its signal-off position.

"Signal threshold" means the combined strength of signal-on indications produced by a plurality of aptamer sensing elements that indicates the presence of a target analyte.

"Time-to-threshold" means the amount of time required for an EAB sensor to reach signal threshold. Such time may be calculated from the initiation of device use, the initiation of sweating, a sensor regeneration time, or other suitable starting point.

"Concentration channel" means a microfluidic channel for collecting, conveying, and concentrating sweat or other biofluid samples from the skin to one or more sensors. The biofluid sample is concentrated relative to one or more target analytes as it moves toward the sensor(s). The sample can be conveyed through the channel by any suitable mechanism for transport, including osmosis or wicking pressures, and may comprise an open channel, paper, textile wicks, or other similar materials.

DETAILED DESCRIPTION OF THE INVENTION

The disclosed invention includes devices and methods for concentrating a sweat or other biofluid sample so that target analytes can be detected using wearable devices employing EAB sensors. With reference to FIG. 1A, a portion of a previously disclosed MCAS EAB sensor is depicted. While the figure depicts, and the discussion focuses on, a single aptamer sensing element, EAB sensors described herein will include a large number (thousands, millions, or billions of individual sensing elements, having an upper limit of $10^{14}/cm^2$) attached to the electrode. The aptamer sensing element 110 includes an analyte capture complex 112, which in turn is comprised of a randomized aptamer sequence 140 that is selected to interact with a target analyte molecule 160, and one or more linker nucleotide sections 142 (one is depicted). The analyte capture complex 112 has a first end covalently bonded to a sulfur molecule, e.g., a thiol 120, which is in turn covalently bonded to an electrode base 130. The electrode 130 may be comprised of gold or another suitable conductive material. The sensing element further includes a redox moiety 150 that may be covalently bonded to a second end of the analyte capture complex 112 or bound to it by a linking section. In the absence of the target analyte, the aptamer 140 is in a first configuration, and the redox moiety 150 is in a first position relative to the electrode 130. When the device interrogates the sensing element using, e.g., square wave voltammetry (SWV), the sensing element produces a first electrical signal, $eT_A$.

Figure 1B:
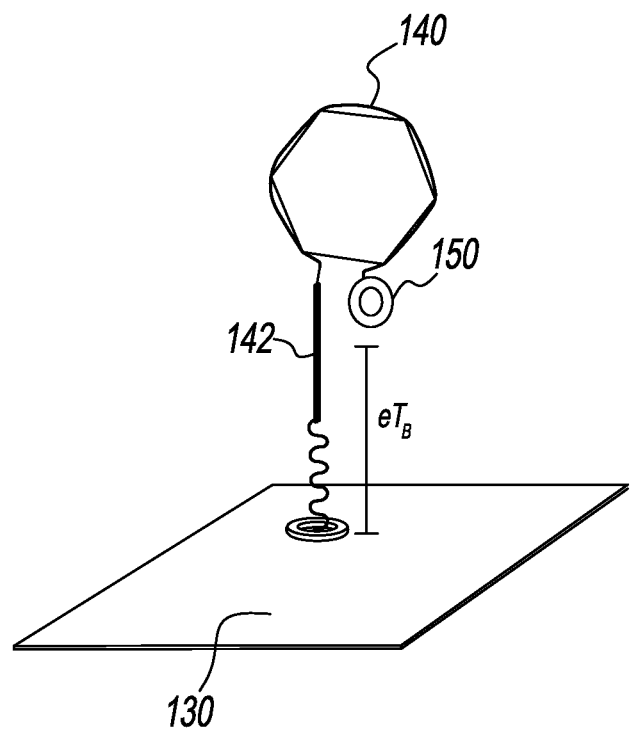

With reference to FIG. 1B, the aptamer 140 is selected to specifically interact with a target analyte 160, so that when the aptamer interacts with a target analyte molecule, the aptamer undergoes a conformation change that partially disrupts the first configuration and forms a second configuration. The capture of the target analyte 160 accordingly moves the redox moiety 150 into a second position relative to the electrode 130. Now when the biofluid sensing device interrogates the sensing element, the sensing element produces a second electrical signal, $eT_B$ that is distinguishable from the first electrical signal. After a recovery interval, the aptamer releases the target analyte, and the aptamer will return to the first configuration, which will produce the corresponding first electrical signal when the sensing element is interrogated.

Analytes existing in biofluid at low concentration, and smaller analytes, however, greatly complicate an EAB sensor's ability to provide reliable, continuous sensing. Concentration ranges for potential target analytes span from μM for hormones, to nM for cortisol, to pM and even fM ranges for larger proteins. When target analyte concentrations are lower, EAB sensors will naturally have fewer capture opportunities, requiring greater sensitivity to ensure that the reduced capture opportunities are fully exploited.

Similarly, small molecule EAB sensors are inherently less stable (and hence produce less reliable signals) than sensors for larger molecules. Target analytes for biofluid sensor applications as contemplated herein may range in size from about 300 Da for hormones to about 15 kDa for microRNA molecules to about 600 kDa for larger proteins to about 1000 kDa for the largest proteins. Other factors being equal, aptamers will generally develop stronger bonds to larger molecules because of the greater number of bonding sites available on such molecules. Further, biofluid sample composition variabilities that tend to reduce bonding strength (such as pH and salinity) will generally have a greater effect on small molecule sensors than they will on larger molecule sensors. In addition, because smaller molecules have fewer binding sites, the difficulties of low concentration detection are even more pronounced for such sensors.

For analytes at low concentrations in biofluid, or for smaller analytes, therefore, it may prove impractical to configure an EAB sensor to perform continuous sensing as described above. For example, a sweat sample may contain so few target analytes so that an insufficient number of molecules will bond with an aptamer, and the device will be unable to resolve a signal indicating a concentration. The analytes that are bound will then release back into solution before another chronologically assured sweat sample can be measured. In such a scenario, while the target analyte is present in sweat, the device will not be able to provide a reliable measurement of the analyte's presence, much less a reliable concentration value.

For certain applications, therefore, it will be necessary to design an EAB sensor device that can provide a qualitative "yes/no" measurement for the presence or absence of an analyte based on an aggregated measurement of biofluid samples taken over time. One solution to this problem is the use of docked-aptamer EAB sensors, as disclosed in U.S. Provisional Application No. 62/523,835. However, such an approach may not always be practical, or may be improved by concentrating a biofluid sample over time with respect to the target analyte. Several configurations for concentrating a biofluid sample to enable detection by various biofluid sensor modalities, to include EAB sensors, were disclosed in PCT/US16/58356. The present disclosure adds additional devices and methods to improve such detection techniques for EAB sensors.

Figure 2:
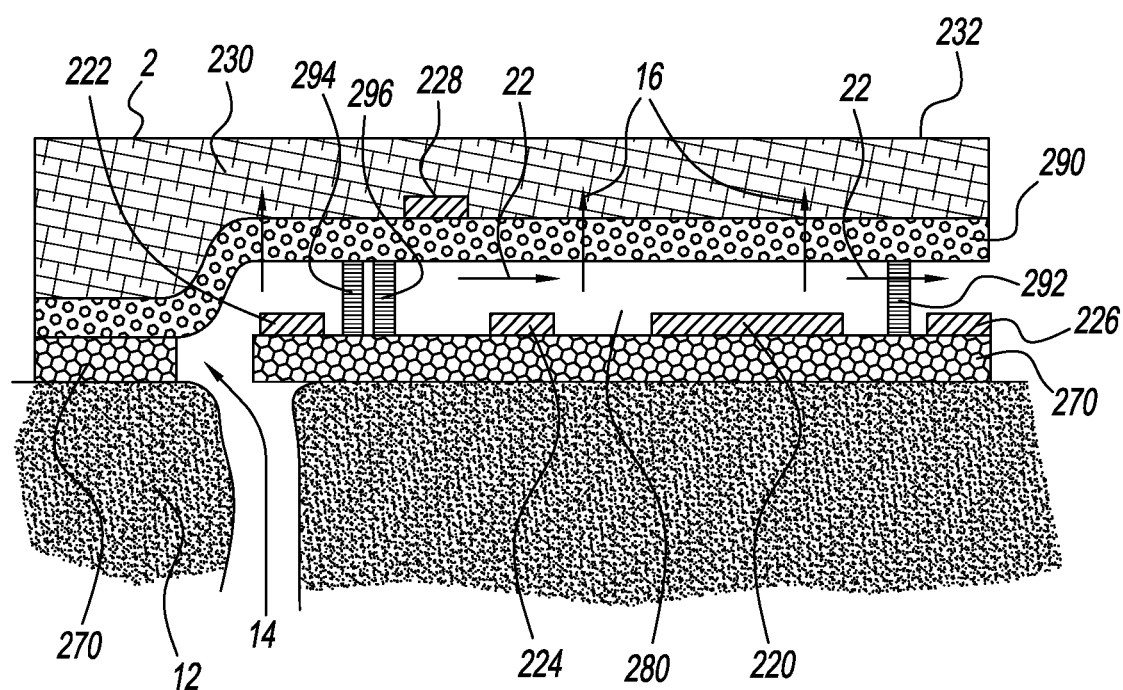
FIG. 2 is a depiction of the disclosed invention with a concentration channel for EAB biofluid sensing.

With reference to FIG. 2, an embodiment is depicted that optimizes sample concentration for a biofluid sensing device with an EAB sensor. The device 2 includes a biofluid-impermeable substrate 270, such as PET, acrylic, glass, or other suitable material, that carries a microfluidic concentration channel 280, one or more EAB sensors 220, a concentration membrane 290, a pump 230, one or more optional secondary sensors 222, 224, 226, 228, an optional post-sensor membrane 292, one or more optional pre-sensor membranes 294, 296, and an optional protective covering 232. Instead of an open concentration channel, some embodiments use a wicking material to transport the biofluid sample from the skin to the EAB sensor(s) 220, where the wicking material is, e.g., paper, a gel, a textile, or a material such as those used in lateral flow assays. The device is placed on skin 12, via an adhesive layer (not shown). Adhesives can be pressure sensitive, liquid, tacky hydrogels, which promote robust electrical, fluidic, and iontophoretic contact with skin. As the biofluid sample 14 enters the device and flows into the concentration channel 280 in the direction of the arrow 22, water (and in some cases untargeted solutes) is drawn through the concentrating membrane 290, and into the pump 230, leaving the target analyte in the concentration channel 280, and effectively concentrating the biofluid sample with respect to the target analyte.

The concentrating membrane is a dialysis membrane, or is an osmosis membrane permeable to ions and impermeable to small molecules and proteins, or may be a membrane that is at least permeable to water and impermeable to the target analyte. For example, a membrane with a 12 kDa molecular mass cutoff will retain solutes that are above 12 kDa, such as human serum albumin, which is 66.5 kDa. The material in the pump 230 may facilitate wicking or osmotic flow, and is a hydrogel, textile, salt, polyelectrolyte solution, or desiccant, such as $MgSO_4$. Depending on the application, the target analyte may be concentrated at least 10×, 100×, or 1000× higher than its original concentration in biofluid. Some embodiments may use the concentrating membrane 290 and pump 230 to maintain the biofluid sample at a pH or salinity level while in the concentration channel.

The optional post-sensor membrane 292, in some embodiments is made from similar material types as used for the concentrating membrane, is configured to pass fluid and solutes smaller than the target analyte, and causes the target analyte to further concentrate near the EAB sensor 220, where measurements are taken. In other embodiments, the post-sensor membrane 292 may simply substantially slow the flow of the biofluid sample through the channel. The optional pre-sensor membrane 294, also made from similar material types as used for the concentrating membrane, filters unwanted solutes, such as molecules larger than the target analyte, from the biofluid sample before it reaches the EAB sensor 220. Some embodiments include more than one pre-sensor membrane 294, 296. The use of multiple pre-sensor membranes allows staged filtering of the biofluid sample. For example, the first pre-sensor membrane is configured to remove large proteins from the biofluid sample, while the second pre-sensor membrane 296 is configured to remove smaller solutes. The plurality of membranes 294, 296 may be configured to filter solutes in various ways, including through electrical charge, osmosis, or other means. Numerous effects upon the sweat sample may be accomplished by using complementary materials for the concentrating membrane, the post-sensor membrane and the pre-sensor membrane(s). For example, one membrane could be an anion exchange membrane, e.g., a modified poly (phthalazinon ether sulfone ketone), and another could be a cation exchange membrane, e.g., nafion or poly(vinyl alcohol)-SiO$_2$, or the membranes could all be dialysis membranes with different mass cutoffs.

In some embodiments, particularly those requiring lengthy sampling times, i.e., a day or longer, the pre-sensor membrane 294 is configured to prevent contamination of the biofluid sample. For example, after a number of hours, proteases in a sweat sample could at least partially consume the target analyte, rendering the target undetectable or introducing error in the measured concentration. Similarly, if certain microbes were allowed to incubate in the concentration channel for several hours, sweat contents may be misinterpreted to include the microbes or their growth byproducts as sweat components. A membrane capable of filtering out proteases, microbes or similar molecules, e.g., modified polyacrylonitrile membranes, may therefore be advantageous for such applications. Other embodiments may include a preservative, such as 0.1% sodium azide or benzamidine, to maintain the integrity of the biofluid sample and its complement of target analyte molecules until sensing is accomplished.

The device is also configured with one or more secondary sensor(s) 222, 224, 226, 228. The biofluid rate sensor(s) may be, for example, a volumetric biofluid flow rate sensor, a galvanic skin response (GSR) sensor, a sweat conductivity sensor, a biofluid conductivity sensor, a skin impedance sensor, a micro-thermal flow sensor, or ion-selective electrode sensors for at least one of $K^+$, $Na^+$ or $Cl^-$. In some embodiments, a secondary sensor 222 measures biofluid flow rate into the device. In use, the device would detect biofluid flow onset and cessation with a GSR sensor, and biofluid flow rate with another sensor, such as a volumetric sensor or conductivity sensor. By tracking the biofluid flow rate, and the time-to-threshold for the EAB sensor 220, the device can back-calculate the analyte's original biofluid concentration.

In other embodiments, secondary sensor(s) 222, 224, 226, 228 are used to assess the amount of biofluid sample concentration, for example, by measuring an increase in concentration of a proxy analyte, such as $K^+$. In various embodiments, the secondary sensors may be inside 222, 224 or outside 226, 228 the concentration channel 280. Within the concentration channel 280, secondary sensors can be located upstream 222 or downstream 224 of membranes 294, 296, or the EAB sensor 220. Outside the channel 280, secondary sensors may be located in the pump 230, or downstream 226 of the EAB sensor. By tracking secondary sensor measurements, the device can determine the amount of biofluid concentration developed. For example, if secondary sensors include $Cl^-$ ISE sensors, the pre-membrane $Cl^-$ sensor 222 measurement can be compared to the pump sensor 228 $Cl^-$ measurement to determine the degree of biofluid concentration across the concentrating membrane 290. Similarly, $Cl^-$ concentration gradients from the pre-filter sensor 222 to the post-filter sensor 224 can be determined. In some embodiments employing flow-rate sensors as secondary sensors, biofluid flow rates through the concentration channel can be measured and tracked as the biofluid moves across the various filter membranes 294, 296, 292 and out of the device. A pump sensor 228 as disclosed may also be used to track the useable lifetime of the device by monitoring the ion content of the material in the pump 230. For example, a pump material having a low NaCl concentration could only move water across the concentrating membrane 290 while the biofluid sample in the channel 280 had a higher NaCl content. Therefore, by tracking the $Na^+$ or $Cl^-$ concentration in the pump material over time, the device could track useable lifespan remaining. Combinations of ISEs, flow rate sensors, and other types of sensors can be used together or separately as contemplated within the invention.

Detection of the target analyte will be positively indicated when a sufficient number of EAB sensing elements captures a target analyte molecule and produces a capture signal when interrogated by the device. The strength of the signal required to indicate the presence of the target in the biofluid sample is known as the signal threshold. Signal threshold will vary by application, and will be set to achieve a desired predictive value that balances false positive indications and false negative indications. Some applications, such as screening the general population for a heart condition, may require very low false positive indications, and therefore would need to have a higher signal threshold, representing greater certainty of analyte presence. Other applications, such as preliminary screening for lead exposure in an at-risk population, may not require such high certainty, and could use a lower signal threshold. In other cases, for example, an EAB sensing element may have an aptamer that relatively weakly binds the target analyte, or the particular biofluid sample may have challenging pH or salinity characteristics, or the target analyte may be very small. In each of these cases, the signal threshold would need to be relatively higher than in the converse case, all other factors being equal.

When a signal threshold is reached for a particular application, the device will have positively detected the presence of the target analyte in biofluid. This provides a qualitative assessment that may be particularly useful for target analytes, such as viral particles, that are not normally present in the body. It may also prove useful for detecting analytes that only emerge in biofluid under special circumstances, e.g., luteinizing hormone upon ovulation, or are upregulated by several factors in the event of a medical condition, e.g., NGAL in for kidney injury.

In other embodiments, the disclosed invention may also be configured to derive a quantitative measurement of target analytes at low concentrations. As a first order estimate of concentration, the device may track the time required to reach the signal threshold, or time-to-threshold. If the device is placed on skin and subsequently reaches the signal threshold within a few minutes, or within a couple of hours, the device can infer that the analyte exists in higher biofluid concentrations than if the time-to-threshold were several hours. For example, if a device configured to determine the presence of inflammation by detecting cytokines takes 5 hours to reach signal threshold, the device may recommend that no action be taken. However, if the device reaches signal threshold after only 2 hours, the device may recommend further action. Similarly, the device could track the volume of biofluid sample required to reach signal threshold. A device that only required 24 µL to reach threshold could be inferred to have a higher concentration of a target analyte than a device that required 90 µL. The device can also provide trending information over multiple concentration cycles, i.e., show whether analyte concentration is changing rapidly, staying the same, or changing slowly. For example, if a device reaches signal threshold after one hour, and then during the subsequent measurement period, reaches signal threshold after 3 hours, the device may infer that the analyte concentration is trending down.

While time-to-threshold or volume-to-threshold assessments can provide a rough first-order estimate of concentration, quantitative measurements would be improved by including biofluid flow rate measurement. In such embodiments, the device measures time-to-threshold and biofluid flow rate to determine the amount of biofluid sample that entered the device. Knowing the volume of the concentration channel, as well as the concentration of analyte within the channel required to reach the signal threshold, the device can estimate the original concentration of the analyte in unconcentrated biofluid.

The disclosed invention improves on existing sensor modalities in a number of ways. For example, lateral-flow assays ("LFA") can aggregate a sample over time and are frequently put forward as potential sensors to detect low concentration molecules. However, LFAs consume water volume and analyte each time they take a measurement and can only be used once. Therefore, interrogating an LFA early may result in a false negative, since the LFA cannot be re-interrogated after additional time. This will bias the user to only interrogate the LFA at the end of the device use cycle. Further, a single LFA cannot provide trend information, and if a device includes multiple LFAs, analyte/sample consumption precludes effectively aggregating their measurements over time, since each LFA will need to receive a separate biofluid sample.

Having to interrogate a biofluid sensing device at the end of the use cycle, and the inability to detect trends, greatly reduces the value of data produced by an LFA device. By contrast, an EAB sensor may make a number of measurements during the use cycle, allowing the device to determine how soon the signal threshold is reached. The EAB device may also detect a decrease in analyte concentration, which may serve as an indication of, for example, the efficacy of a drug or other treatment regimen. For instance, a device configured to track a wearer's hydration levels detects vasopressin after one hour of use, indicating a dehydrated state, and prompting the user to drink a recommended amount of fluid. When the device takes another reading at the second hour of use, and detects no vasopressin, the user may infer that the fluid intake effectively treated the dehydration.

Figure 3:
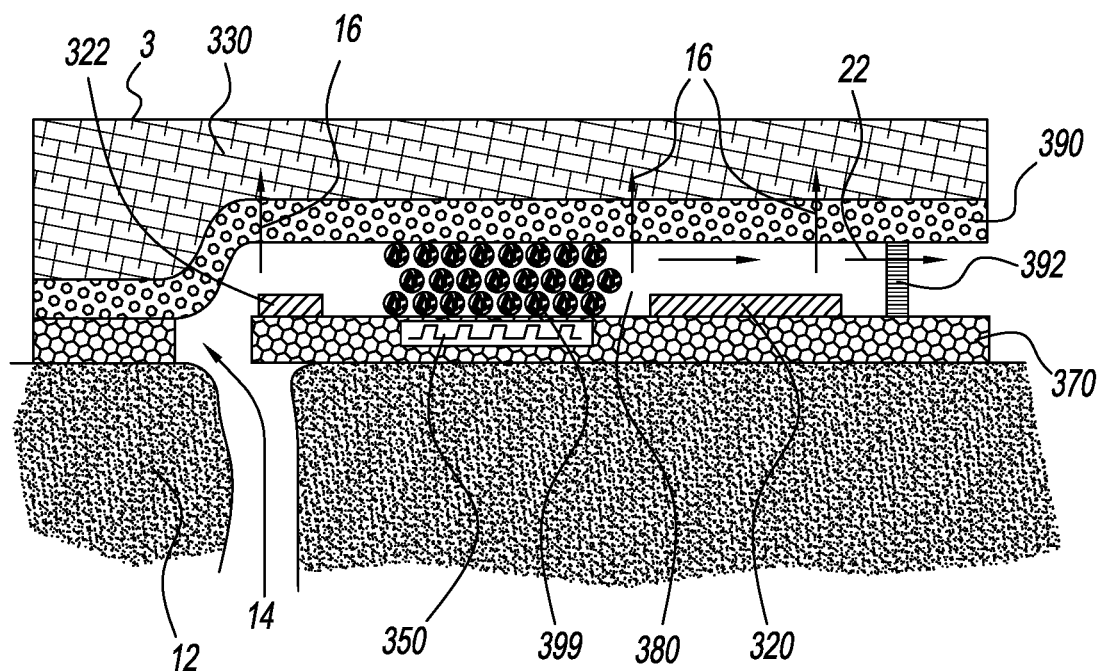
FIG. 3 is a depiction of the disclosed invention with a concentration channel for EAB biofluid sensing.

With reference to FIG. 3, where like numbers represent like components of previous figures, an alternate embodiment of the device depicted in FIG. 2 is presented. This embodiment includes a concentration channel 380 configured as a column containing a functionalized substrate in place of the one or more pre-sensor membranes 294, 296 of FIG. 2. The substrate is, for example, a plurality of spherules 399, e.g., silica, gel, resin, or polymer beads immobilized within the microfluidic channel 380, or can be another suitable arrangement providing high surface area and minimal flow resistance, such as through techniques used in chromatography methods. The spherules 399 are configured to maximize the surface area available to filter out or slow unwanted biofluid solutes while allowing target analyte molecules to pass through, or pass through at a faster pace, to the sensor(s) 320. The plurality of spherules may function as a filter simply through the size of the gaps among or within the spherules, e.g., larger proteins take longer to pass through the substrate, while smaller solutes pass through rapidly to the sensor 320. Alternately, smaller solutes may pass through rapidly away from the sensor(s) 320, allowing improved measurement of the remaining larger analyte molecules. In some embodiments, the disclosed substrate is used to sort solutes by size, allowing the device to more easily measure different target analytes of different sizes, e.g., by locating sensors within the channel based on where their respective target analytes are expected to emerge from the substrate. Other embodiments may include spherules with various functionalized coatings, e.g., dextran, antibodies, aptamers, charged particles, etc., to facilitate size or charge filtering. In some embodiments, spherules may be electrically neutral, charged, or magnetized. Embodiments employing a substrate filter may provide operational advantages over membrane filters by allowing the device to pre-filter the biofluid sample without imposing excessive backpressure on the sample, which can inhibit continuous or chronologically assured sampling.

Rather than serving as a filter, some embodiments will include a functionalized substrate designed to capture one or more target analytes. In these embodiments, the spherules may be coated with antibodies or aptamers that are configured to capture target analytes in the biofluid, for example, the spherules may be coated with aptamers for capturing cortisol. As target analyte molecules collect on the substrate, back pressure will gradually build as the substrate become impassible to new biofluid. Therefore, some embodiments of the device include a local heater 350 configured to cause solutes to release from the substrate. The heater may produce, e.g., radiant heat, LED light of specified wavelengths, high frequency vibrations, electrical charge oscillations, or other similar outputs for removing solutes from the substrate. In use, the device activates the heater 350, which causes a release of a group of captured analyte molecules, which then flow through the substrate to the EAB sensor 320, where they are detected. As with other embodiments, the device can make a qualitative measurement, when/if the target analyte is present in enough quantity to reach the EAB sensor's signal threshold. Or, based on the amount of time and the sweat rate required to reach signal threshold, a qualitative measurement can also be acquired. The local heater 350 as described may also be used in embodiments where the substrate serves as a filter. When biofluid solutes build up in the gaps among substrate components, the device activates the heater to cause the solutes to release from the substrate so that flow through the device is maintained or restored.

Figure 4:
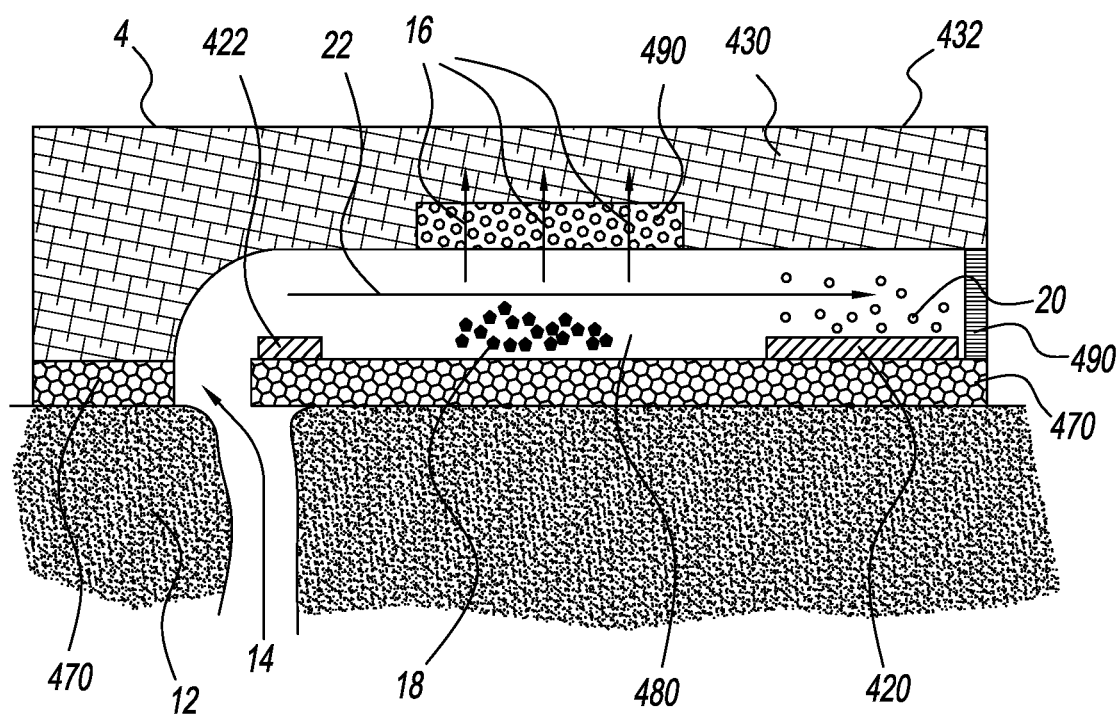
FIG. 4 depicts an embodiment of the disclosed invention with a concentration channel for EAB biofluid sensing.

With reference to FIG. 4, another embodiment of the present disclosure is configured to facilitate the detection of larger molecules, such as proteins. The device 4 includes a biofluid-impermeable substrate 470, a concentration channel 480, one or more EAB sensors 420, one or more optional secondary sensors 422, a concentrating membrane 490, an optional post-sensor membrane 492, one or more optional pre-sensor membranes (not shown), and a pump 430. In this embodiment, the EAB sensor 320 is located a distance downstream from the membrane 490, e.g., greater than 100 µm, or greater than 1 cm. As the biofluid sample 14 enters the device and flows into the concentration channel 480 in the direction of the arrow 22, water 16 is drawn through the membrane 490, and into the pump 430. The concentrating membrane filters out the target analyte 20, as well as several larger molecules 18, all of which stay in the concentration channel 480. However, because of their relative abundance in biofluid, certain larger proteins, such as dermcidin and albumin in sweat, will aggregate at the floor of the channel in the vicinity of the filter. If the EAB sensor 420 were located too close to the membrane, the aggregating proteins would accumulate on top and foul the sensor. Therefore, by locating the EAB sensor a distance away, for example 2 mm, 5 mm, or 1 cm in the direction of flow 22, the relatively lower concentration target analyte can diffuse into the biofluid sample and migrate down to the EAB sensor 420. Note that this may be less of a consideration for small molecule detection, since even if an EAB sensor is fouled by large proteins, a smaller target analyte might be able to pass through the accumulated debris and still reach the EAB sensor.

Figure 5A:
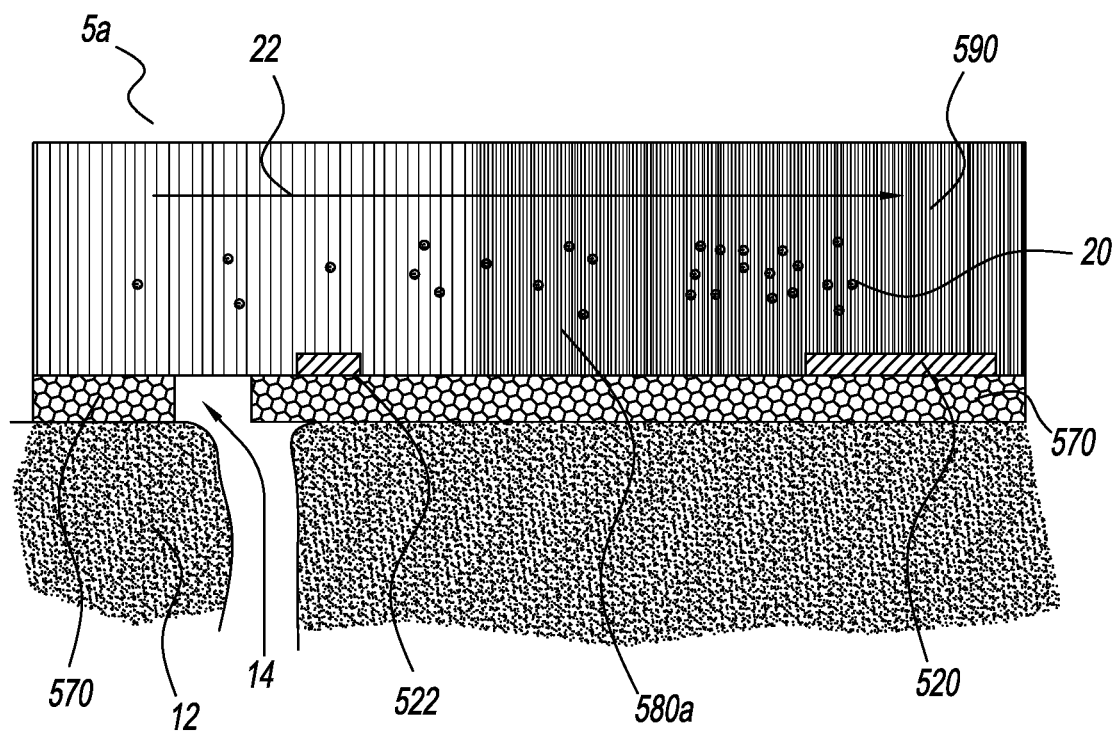
FIG. 5 is a depiction of the disclosed invention with a concentration channel for EAB biofluid sensing.

With reference to FIG. 5A, an embodiment of the disclosed invention may include a variable density gel 590 (or other medium with similar properties) within the concentration channel 580A. The medium increases in density or has pores that decrease in size in the direction of the fluid flow 22. The material can be tuned to correlate with the size, i.e., molecular weight, of the target analyte 20. As a biofluid sample flows through the medium, heavier solutes, or solutes that are larger than the pores, will move slower than the biofluid flow rate. As solute flow rates slow relative to the biofluid flow rate, the target analyte 20 will gradually become concentrated in the direction of flow 22, at which point the EAB sensor 520 can take measurements to detect the analyte 20.

Figure 5B:
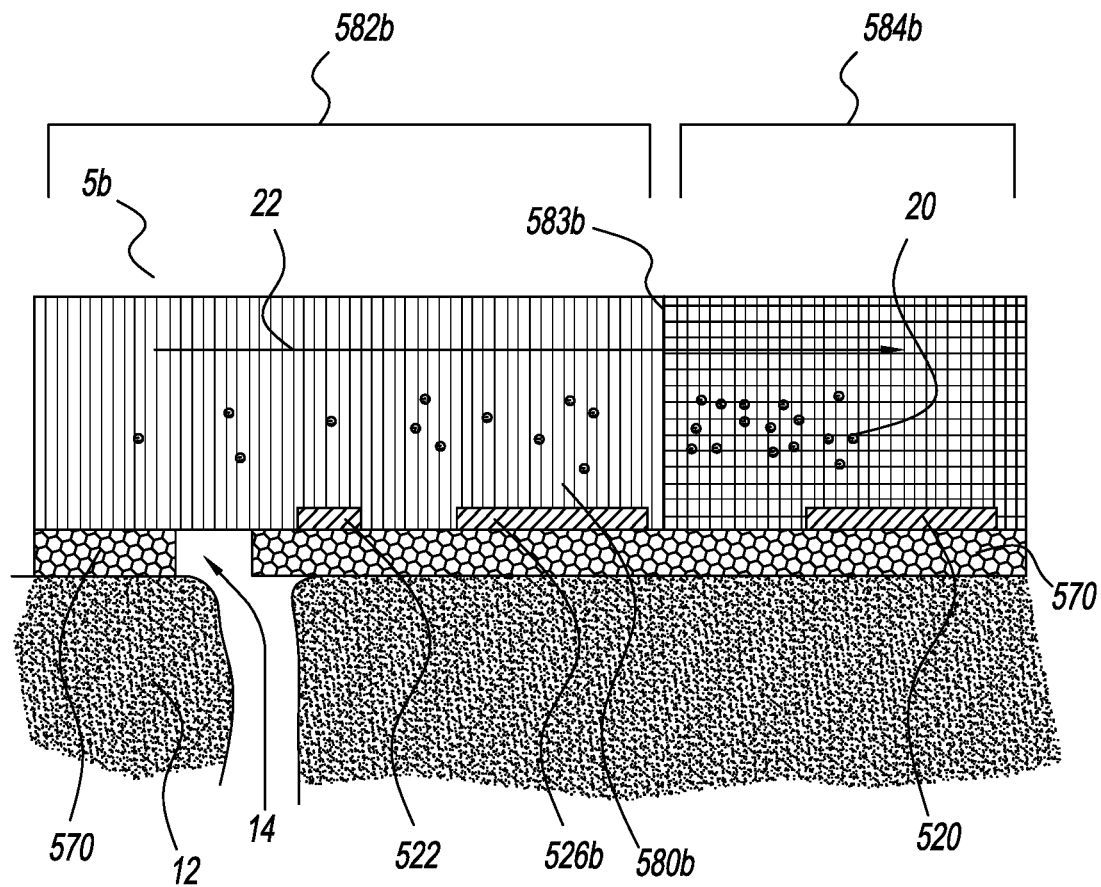

Similarly, the embodiment depicted in FIG. 5B includes within the concentration channel 580B two or more gels (or other media with similar properties) with increasing densities in the direction of flow 22. A first section 582B has a first density, and a second section 584B has a second, greater density. Step edges of increasing density are thereby created at the boundaries 583B (one is depicted) between the sections. As a biofluid sample flows through the concentration channel 580B, the target analyte 20 will concentrate at the boundary 583B and then move at a slower rate in the next section. The result is a "wave front" in the channel in which the analyte 20 is concentrated relative to unconcentrated biofluid, and can be detected by EAB sensor 520. In some embodiments, additional EAB sensors 526B (one shown) may be provided so that each section has an EAB sensor to measure the concentration of analyte retained in that section, or to allow back-calculation of the original analyte concentration in the biofluid. Alternately, each section can be tuned to retain a different target analyte, so the EAB sensor 520 and additional EAB sensor 526B measure different analytes.

Figure 6:
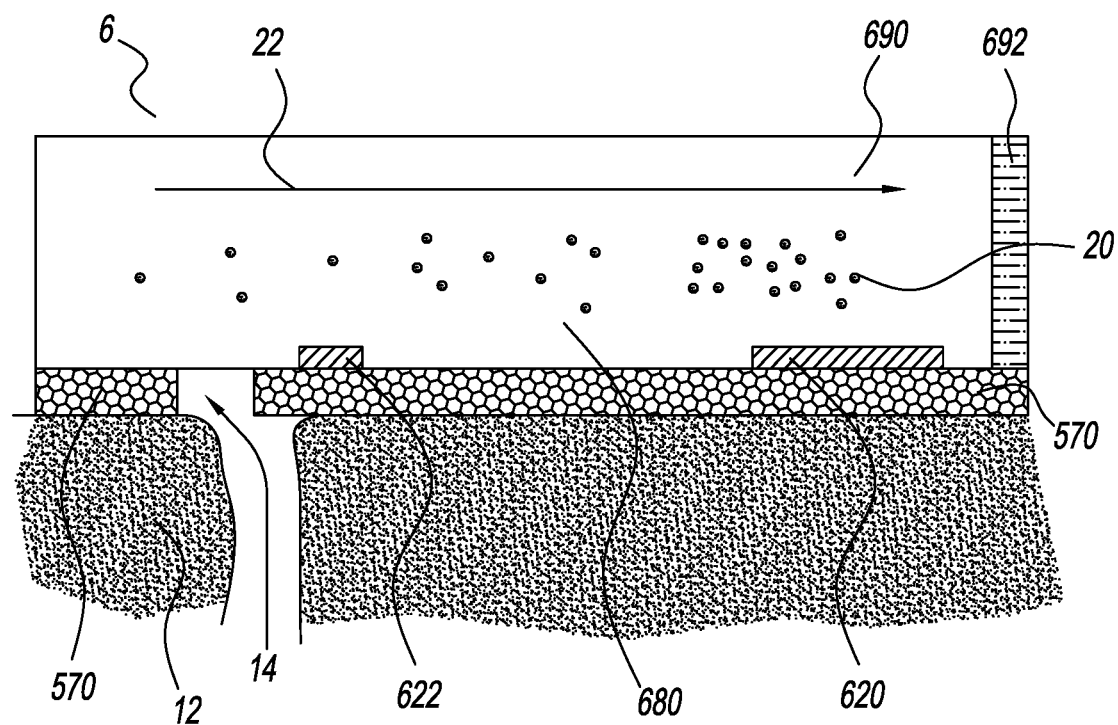
FIG. 6 is a depiction of the disclosed invention with a concentration channel for EAB biofluid sensing.

With reference to FIG. 6, where like numbers refer to like features in previous figures, another embodiment of the present disclosure is presented that represents a simplified means of biofluid sample concentration for EAB sensor devices. In this embodiment, as a sweat sample 14 enters the concentration channel 680 and begins to flow in the direction of the arrow 22, the sweat sample encounters a post-sensor membrane 692. In some embodiments, the post-sensor membrane is configured to pass fluid and solutes smaller than the target analyte 20, which causes the target analyte to concentrate near the EAB sensor 620. In other embodiments, the post-sensor membrane 692 may simply substantially slow the flow of the biofluid sample through the channel, which effectively concentrates the target analyte 20 near the EAB sensor 620. Some embodiments include one or more optional secondary sensors 622, or one or more optional pre-sensor membranes (not shown).

Devices may be further configured for improved performance low-concentration detection. For example, the sensors may be electromagnetically shielded to reduce the effects of electrical noise, thereby improving sensitivity. Similarly, an EAB sensing element may be surrounded by neutral pH fluid to improve sensitivity for low concentration analytes.

This has been a description of the disclosed invention along with a preferred method of practicing the disclosed invention, however the invention itself should only be defined by the appended claims.

What is claimed is:

1. A biofluid sensing device configured to be worn on skin and providing biofluid sample concentration for electrochemical aptamer-based (EAB) sensor detection of analytes, the biofluid sensing device comprising:
   a biofluid-impermeable substrate configured to be positioned over the skin;
   one or more EAB sensors for measuring a characteristic of an analyte in a biofluid sample, the one or more EAB sensors positioned over a surface of the biofluid-impermeable substrate;
   a channel for concentrating the biofluid sample with respect to the analyte, wherein the channel is configured to route the biofluid sample from a first end of the channel and towards a second end of the channel, and wherein the analyte in the biofluid enters the biofluid sensing device at a first molarity and is concentrated to a second molarity, the second molarity being greater than or equal to a signal threshold of the EAB sensor;
   one or more selectively permeable membranes positioned relative to the channel; and
   one or more secondary sensors positioned over a surface of the biofluid-impermeable substrate or over a surface of one of the one or more selectively permeable membranes.

2. The biofluid sensing device of claim 1, wherein the one or more selectively permeable membranes are one or more of the following: a pre-sensor membrane positioned between the first end of the channel and the one or more EAB sensors; a post-sensor membrane positioned between the second end of the channel and the one or more EAB sensors; and a concentrator membrane, the concentrator membrane having a first surface adjacent to the channel and a second surface opposite the channel.

3. The biofluid sensing device of claim 2, further comprising a pump, positioned adjacent to the second surface of the concentrator membrane.

4. The biofluid sensing device of claim 1, wherein the one or more secondary sensors include one or more of the following: a volumetric biofluid flow rate sensor; a microthermal flow rate sensor; a galvanic skin response (GSR) sensor; a skin capacitance sensor; a biofluid conductivity sensor; and an ion-selective electrode sensor for one or more of $K^+$, $Na^+$, and $Cl^-$.

5. The biofluid sensing device of claim 1, wherein at least one of the one or more secondary sensors is positioned at one or more of the following positions: between the first end of the channel and a selectively permeable membrane of the one or more selectively permeable membranes; between the first end of the channel and the one or more EAB sensors; between a selectively permeable membrane of the one or more selectively permeable membranes and the second end of the channel; and adjacent to a surface of a selectively permeable membrane of the one or more selectively permeable membranes that is adjacent to the channel.

6. The biofluid sensing device of claim 1, further comprising: a functionalized substrate positioned between the first end of the channel and the one or more EAB sensors.

7. The biofluid sensing device of claim 6, wherein the functionalized substrate is a plurality of spherules.

8. The biofluid sensing device of claim 6, wherein the functionalized substrate includes one of the following: a dextran coating; an antibody coating; an aptamer coating; a charged particle coating; an electrically neutral charge; an electrically positive charge; an electrically negative charge; and a magnetic polarity.

9. The biofluid sensing device of claim 6, wherein at least one secondary sensor of the one or more secondary sensors is positioned between the first end of the channel and the functionalized substrate.

10. The biofluid sensing device of claim 6, further comprising a heater positioned adjacent to the functionalized substrate.

11. The biofluid sensing device of claim 2, wherein the concentrator membrane is positioned relative to the one or more EAB sensors such that, the position of the concentrator membrane substantially prevents a decrease in performance of the one or more EAB sensors caused by solutes precipitating out of the biofluid sample and settling on a sensor surface.

12. The biofluid sensing device of claim 1, wherein the channel contains a concentration gel, the concentration gel having a first density at the first end of the channel, and a second density at the second end of the channel, wherein the second density is greater than the first density.

13. The biofluid sensing device of claim 12, wherein the concentration gel increases in density substantially continuously from the first end of the channel to the second end of the channel.

14. The biofluid sensing device of claim 12, wherein the concentration gel is comprised of a plurality of sections, and one or more boundaries between each of the plurality of sections, wherein each of the plurality of sections has a gel density and the plurality of sections is arranged so that the gel densities increase from the first end of the channel to the second end of the channel.

15. The biofluid sensing device of claim 1, wherein the channel contains a concentration material having a plurality of pores, wherein the plurality of pores have a first size at the first end of the channel, and a second size at the second end of the channel, wherein the second size is smaller than the first size.

16. The biofluid sensing device of claim 15, wherein the plurality of pores decrease in size continuously from the first end of the channel to the second end of the channel.

17. The biofluid sensing device of claim 15, wherein the concentration material is comprised of a plurality of sections, each section including a plurality of pores, wherein a boundary is positioned between each section of the plurality of sections, wherein each section has a pore size and wherein the plurality of sections are arranged within the channel such that the pore size in each section increases from the first end of the channel to the second end of the channel.

18. The biofluid sensing device of claim 1, wherein the biofluid sample is one of the following: sweat, interstitial fluid, blood, plasma, serum, tears, and saliva.

19. A method of using the biofluid sensing device of claim 1, the method comprising:
receiving, at the first end of the channel of the biofluid sensing device, a biofluid sample that includes a target analyte at a first molarity;
concentrating the biofluid sample as the biofluid is routed toward the second end of the channel, wherein concentrating the biofluid sample causes the molarity of the analyte to transition from the first molarity to a second molarity, the second molarity being greater than or equal to a signal threshold of the one or more EAB sensors;
obtaining, using the one or more EAB sensors, a measurement of a characteristic of the target analyte; and
outputting the characteristic of the target analyte.

20. The method of claim 19, wherein the characteristic of the target analyte is a concentration estimate of the biofluid sample.

21. The method of claim 19, further comprising determining a time-to-threshold that is a duration of time from between when the biofluid sensing device is operating on skin and when the signal threshold is reached.

22. The method of claim 19, further comprising determining a factor by which the second molarity is greater than the first molarity.

23. The method of claim 19, wherein the second molarity is greater than the first molarity by at least one of the following factors: 10; 100; and 1000.

* * * * *